(12) United States Patent
Nobis et al.

(10) Patent No.: US 12,076,572 B2
(45) Date of Patent: Sep. 3, 2024

(54) DEVICE FOR SUPPLYING ENERGY TO AN ACTIVE EYE IMPLANT

(71) Applicants: Carl Zeiss AG, Oberkochen (DE); Carl Zeiss Jena GmbH, Jena (DE)

(72) Inventors: Thomas Nobis, Leipzig (DE); Tobias Schmitt-Manderbach, Kempten (DE); Matthias Hillenbrand, Jena (DE); Petr Vojtisek, Jena (DE)

(73) Assignees: Carl Zeiss AG, Oberkochen (DE); Carl Zeiss Jena GmbH, Jena (DE)

( * ) Notice: Subject to any disclaimer, the term of this patent is extended or adjusted under 35 U.S.C. 154(b) by 513 days.

(21) Appl. No.: 17/601,063

(22) PCT Filed: Apr. 2, 2020

(86) PCT No.: PCT/EP2020/059409
§ 371 (c)(1),
(2) Date: Oct. 2, 2021

(87) PCT Pub. No.: WO2020/201427
PCT Pub. Date: Oct. 8, 2020

(65) Prior Publication Data
US 2022/0203106 A1   Jun. 30, 2022

(30) Foreign Application Priority Data
Apr. 3, 2019 (DE) .................. 102019108678.7

(51) Int. Cl.
*G02C 11/00* (2006.01)
*A61N 1/378* (2006.01)
(Continued)

(52) U.S. Cl.
CPC ......... *A61N 1/3787* (2013.01); *G02B 6/4215* (2013.01); *G02B 26/0816* (2013.01);
(Continued)

(58) Field of Classification Search
CPC .............. A61N 1/3787; A61N 1/36046; G02B 6/4215; G02B 26/0816; G02B 26/10;
(Continued)

(56) References Cited

U.S. PATENT DOCUMENTS 6,915,062 B2   7/2005   Hulse et al.
7,008,099 B2   3/2006   Yamashita et al.
(Continued)

FOREIGN PATENT DOCUMENTS

CN   105281003 A   1/2016
DE   10315397 A1   10/2004
(Continued)

OTHER PUBLICATIONS

International Search Report rendered by the International Searching Authority for PCT/EP2020/059409, dated Jun. 29, 2020, 2 pages.
(Continued)

*Primary Examiner* — Tuyen Tra
(74) *Attorney, Agent, or Firm* — Skaar Ulbrich Macari, P.A.

(57) ABSTRACT

An apparatus for supplying energy to an active eye implant can include a beam expander that includes a first expansion element and a second expansion element. The second expansion element can be configured to provide light that has been expanded twice and is effectively focused. A processes for manufacturing apparatuses for supplying energy to an active eye implant can be based on head geometry data of a user.

23 Claims, 12 Drawing Sheets

(51) Int. Cl.
  *G02B 6/42* (2006.01)
  *G02B 26/08* (2006.01)
  *G02B 26/10* (2006.01)
  *G02B 27/09* (2006.01)
  *H02J 50/30* (2016.01)

(52) U.S. Cl.
  CPC ......... *G02B 26/10* (2013.01); *G02B 27/0916* (2013.01); *G02C 11/10* (2013.01); *H02J 50/30* (2016.02)

(58) Field of Classification Search
  CPC ..... G02B 27/0916; G02C 11/10; H02J 50/30; H02J 2310/23; H02J 50/005
  USPC .................................................. 351/41, 158
  See application file for complete search history.

(56) References Cited

U.S. PATENT DOCUMENTS

| | | |
|---|---|---|
| 7,729,572 B1 | 6/2010 | Pepper et al. |
| 8,320,032 B2 | 11/2012 | Levola |
| 8,377,120 B2 | 2/2013 | Lipshitz et al. |
| 9,084,564 B2 | 7/2015 | Bublitz et al. |
| 9,248,309 B2 * | 2/2016 | Pugh .................. A61N 5/0601 |
| 9,474,902 B2 * | 10/2016 | Gefen .................. G02B 27/017 |
| 9,901,748 B2 * | 2/2018 | Geyer .................. A61N 5/062 |
| 10,831,031 B2 | 11/2020 | Rudolph et al. |
| 10,983,338 B2 | 4/2021 | Hegyi |
| 11,137,531 B2 | 10/2021 | Singer et al. |
| 11,624,918 B2 | 4/2023 | Dobschal |
| 2002/0149924 A1 | 10/2002 | Falicoff et al. |
| 2002/0186919 A1 | 12/2002 | Pepper |
| 2005/0286266 A1 | 12/2005 | Park |
| 2006/0028726 A1 | 2/2006 | Ushigome |
| 2006/0126179 A1 | 6/2006 | Levola |
| 2010/0231693 A1 | 9/2010 | Levola |
| 2012/0013962 A1 | 1/2012 | Subbaraman et al. |
| 2014/0140091 A1 | 5/2014 | Vasylyev |
| 2014/0232651 A1 | 8/2014 | Kress et al. |
| 2014/0376207 A1 | 12/2014 | Futterer |
| 2015/0049509 A1 | 2/2015 | Meyers et al. |
| 2015/0182748 A1 | 7/2015 | Gefen et al. |
| 2016/0070113 A1 | 3/2016 | Travis |
| 2016/0231567 A1 | 8/2016 | Saarikko et al. |
| 2016/0231568 A1 | 8/2016 | Saarikko et al. |
| 2017/0160548 A1 | 6/2017 | Woltman et al. |
| 2017/0205618 A1 | 7/2017 | Basset et al. |
| 2018/0067318 A1 | 3/2018 | St. Hilaire |
| 2018/0232048 A1 | 8/2018 | Popovich et al. |
| 2018/0364409 A1 | 12/2018 | Lee et al. |
| 2019/0046798 A1 | 2/2019 | Kindt et al. |
| 2019/0187465 A1 | 6/2019 | Erler et al. |
| 2019/0204594 A1 | 7/2019 | Hegyi |
| 2019/0391377 A1 | 12/2019 | Stoppe et al. |
| 2020/0103675 A1 | 4/2020 | Schwarz et al. |
| 2022/0019091 A1 | 1/2022 | Nobis et al. |
| 2022/0203105 A1 | 6/2022 | Nobis et al. |
| 2022/0206208 A1 | 6/2022 | Hillenbrand et al. |

FOREIGN PATENT DOCUMENTS

| | | |
|---|---|---|
| DE | 102017130344 A1 | 6/2019 |
| GB | 2411248 A | 8/2005 |
| JP | 2017156389 A | 9/2017 |
| KR | 20150065137 A | 6/2015 |
| WO | 2015101932 A2 | 7/2015 |
| WO | 2015151255 A1 | 10/2015 |
| WO | 2015167492 A1 | 11/2015 |
| WO | 2016149416 A1 | 9/2016 |
| WO | 2017180403 A1 | 10/2017 |
| WO | 2018204712 A1 | 11/2018 |

OTHER PUBLICATIONS

Written Opinion rendered by the International Searching Authority for PCT/EP2020/059409, dated Jun. 29, 2020, 4 pages.
Office Action to a parallel Japanese Patent Application rendered by the Japan Patent Office on Feb. 20, 2024, 17 pages (including summary English translation).
Office Action to a parallel (U.S. Appl. No. 17/600,857) rendered by the United States Patent and Trademark Office on Mar. 21, 2024, 16 pages.
Office Action to a parallel (U.S. Appl. No. 17/600,857) rendered by the United States Patent and Trademark Office on Jan. 9, 2024, 14 pages.
Office Action to the corresponding German Patent Application rendered on Feb. 29, 2020, 14 pages (including partial English translation).
Office Action to a parallel European Patent Application rendered by the European Patent Office (EPO) on Jun. 12, 2023, 10 pages (including English translation).
Office Action to a parallel (U.S. Appl. No. 17/600,857) rendered by the United States Patent and Trademark Office on Jul. 6, 2023, 16 pages.
Office Action to a parallel Japanese Patent Application rendered by the Japan Patent office on Sep. 5, 2023, 18 pages (including summary English translation).
International Search Report (and its English-language translation) from parallel International Patent Application No. PCT/EP20/59118, dated Jul. 20, 2020, 9 pages.
Written Opinion (and its English-language translation) from parallel International Patent Application No. PCT/EP20/59118, dated Jul. 20, 2020, 11 pages.
International Search Report (and its English-language translation) from parallel International Patent Application No. PCT/EP2020/059407, dated Jun. 24, 2020, 5 pages.
Written Opinion (and its English-language translation) from parallel International Patent Application No. PCT/EP2020/059407, dated Jun. 24, 2020, 10 pages.
Search Report (and its English-language translation) from German Application No. DE 10 2019 108 679.5, dated Dec. 12, 2019, 10 pages.
Search Report (and its English-language translation) from German Application No. DE 10 2019 108 678.7, dated Dec. 11, 2019, 11 pages.

* cited by examiner

DEVICE FOR SUPPLYING ENERGY TO AN ACTIVE EYE IMPLANT

PRIORITY

This application claims the priority of German patent application DE 10 2019 108 678.7, filed Apr. 3, 2019, which is hereby incorporated herein by reference in its entirety.

FIELD

The present application relates to devices and methods for supplying power to an active ocular implant by means of light.

BACKGROUND

Active ocular implants are devices which are implanted into an eye of a patient in order to carry out certain functions there. Retinal implants are examples of such active ocular implants. Retinal implants have been developed to restore vision, at least to a certain degree, for persons who have lost the ability to see but who still have a connection from the optic nerve to the brain. Such retinal implants usually comprise an image sensor which produces—optionally with additional circuits—electric pulses that are then registered via the optic nerve.

Other examples of active ocular implants are actively accommodating intraocular lenses or implanted sensors for measuring parameters in the eye, for example the blood sugar level in the aqueous humor. In contrast to passive implants (e.g., simple lenses), such active ocular implants require electric energy in order to be operated.

One option for the energy supply lies in the supply of light, for example infrared radiation below the visible range, which is then converted into electric energy by the active ocular implant, essentially by means of a solar cell or a similar device. However, a supply with other light wavelengths is also possible as a matter of principle.

The power transferred by the radiation may also serve for communication with the active ocular implant, for example by modulating the intensity and/or frequency of the transferred radiation.

Some devices and methods for supplying an active ocular implant are described in the documents DE 10 2016 103 285 A1 and DE 10 2017 107 346 A1.

An interface between external optical systems for supplying an active ocular implant and the human eye with the relevant implant must meet a number of requirements. By way of example, these are based on anatomical features of the human eye, on the usual viewing habits in the considered case or on the demands relating to the harmlessness of the utilized radiation to health.

Depending on the application, the requirements specified below in respect of a power supply system for an active ocular implant come into question on an individual basis or in combination.

It is desirable for a power supply system, which is installed in a spectacle frame for example, to operate reliably even in the case of positioning inaccuracies of the spectacle frame. To this end, for example, robustness in relation to a lateral offset of the eye with respect to the optical system and/or robustness in relation to an axial offset of the eye with respect to the optical system are/is desirable.

Further, it is desirable for the power supply system to be insensitive to physiological processes, for example have a robustness in relation to variations in the size of the eye pupil and/or robustness in relation to variations of the angle of rotation of the eye in the eye socket. Expressed differently, the power supply of the ocular implant should be ensured in the case of different rotation angles or pupil sizes.

Further, high efficiency of the light made available is desirable, i.e., as far as possible exclusive illumination of the light receiver or receivers with little overexposure, in order to ensure a good supply and reduce the power requirements of the system, for example in view of portable systems.

SUMMARY

It is an object of certain embodiments to provide improved devices and methods for supplying an active ocular implant over a large angle range.

According to a first aspect of certain embodiments, an device with a spectacle lens is provided for supplying power to an active ocular implant in an eye of a user. The device comprises in certain embodiments:
 a light source,
 a beam expander which is arranged in or on the spectacle lens and comprises a first expansion element and a second expansion element.

In this case, the device is set up to input couple light from the light source into the spectacle lens and guide said light to the first expansion element.

The first expansion element is further set up to receive the light, expand said light along a first direction and guide at least some of the light as expanded light in a second direction to the second expansion element. In this case, the second direction differs from the first direction.

The second expansion element is set up to receive the expanded light, expand said expanded light along the second direction and provide said expanded light as twice expanded light in a third direction via an emission surface, wherein the third direction at least partly does not extend in the spectacle lens.

The second expansion element is further set up to effectively focus the twice expanded light.

Various optical elements mentioned above and below, for example the first and second expansion element, but also optical elements mentioned below, can be embodied as linear gratings with changeable dimensions. They can also be embodied as volume holograms, for example as multiply exposed volume holograms, and/or as gratings, for example as surface gratings, for example as segmented surface gratings.

There are numerous further options for realizing such optical elements. By way of example, mirrors can be used as well. By way of example, such mirrors can be embedded into the spectacle lens in an arrangement, for example as a regular or irregular array.

In the case of some optical elements a focusing effect can be generated directly by the element itself, for example in the case of volume holograms or curved mirrors or distorted gratings. In the case of other optical elements, a combination with further optical elements, for example lenses, is possible in order to obtain effective focusing.

The respective optical elements can overlap in part or in full in some embodiments of the optical elements. By way of example, first and second expansion element can be arranged in part or in full in the same volume of the spectacle lens. A projected partial or complete overlap is also possible, for example by virtue of one grating being arranged on a front side of a waveguide and a second grating being arranged on a back side of a waveguide, wherein the waveguide may be part of the spectacle lens and first and second grating appear to overlap from a certain direction, for example in the case of a straight gaze through the spectacle lens, even though they are arranged in different volumes of the spectacle lens.

Optical elements may be buried in part or in full in the spectacle lens, i.e., be surrounded in part or in full by material of the spectacle lens.

Beam expanders that operate on the basis of volume holograms are known in their own right, for example from DE 10 2016 115 938 A1 or US 2016/0231568 A1, for a different purpose, specifically in devices for mirroring-in data, and are referred to as pupil expanders. However, such known beam expanders serving to mirror-in data do not offer any effective focusing but collimated or divergent light in order to facilitate a sharp image representation of pixels representing the mirrored-in data.

By contrast, for supplying power to active ocular implants it is not always necessary to ensure a sharp image representation of individual pixels. Consequently, the known beam expanders can be modified in such a way that they bring about effective focusing as described below and above.

Such beam expanders may be advantageous in that the beam expanders allow a large angle range to be illuminated so that the power supply of the active ocular implant is robustly ensured, for example in the case of the above-described physiological processes such as rotation of the eye and/or positioning inaccuracies of the device. As a result of the effective focusing, the beam expanders can further have the advantage of further improving the power supply of the active ocular implant, for example in the case of changes in pupil size.

In this case, directions are understood to mean effective directions which need not characterize a direction of propagation of individual photons or waves but which can characterize a general, possibly averaged direction of propagation of the respective light. By way of example, if the propagation in the second direction in the spectacle lens is implemented by means of total-internal reflection, the second direction describes the direction of propagation in the spectacle lens and not the light path of individual, reflected rays. The same applies accordingly to the other directions specified above and below.

Effective focusing within the scope of this application is understood to mean that the twice expanded light is steered to an imaginary focal surface between emission surface and the active ocular implant along the third direction, wherein the imaginary focal surface is smaller than the emission surface.

The light source may be an infrared light source. An infrared light source can preferably substantially emit only (i.e., for example, apart from unwanted effects, e.g., incomplete filtering) in the infrared range with wavelengths above 780 nm so as not to interfere with the perception of visible light.

The device can be an device that is worn on the head; by way of example, the device can be a pair of spectacles. The device may also comprise a plurality of components, for example the device can comprise a pair of spectacles and a supply device which are coupled to one another. By way of example, the light source can be arranged in the supply device and the light can be transmitted to the pair of spectacles by means of a light guide. However, other embodiments of the device are also possible.

The first expansion element and/or the second expansion element and/or further expansion elements, as described below, and/or an input coupling element, as described below, can be or comprise a volume hologram and/or a grating, for example a surface grating.

The first expansion element and/or the second expansion element and/or further expansion elements, as described below, and/or an input coupling element, as described below, can have a series arrangement or a tree structure arrangement.

In this context, a tree structure arrangement of the relevant elements is understood to mean that light is transmitted from at least one element or region of an element to at least two different elements or regions. Expressed differently, there can be branching of the light.

In this case, different branches can be provided, in general $y^n$, where y is the number of initial light beams or the number of initial light beams −1.

A combination of various such arrangements is also possible, for example a tree structure can be present first and optical elements or regions can then in turn be combined in a series structure within an individual branch of the tree structure.

The beam expander can comprise a third expansion element, wherein the first expansion element is further set up to guide a further portion of the light as expanded light to the third expansion element in a fourth direction, wherein the fourth direction differs from the first, second and third direction, and wherein the third expansion element is set up to receive the further portion of the expanded light, expand said expanded light along the fourth direction and provide said expanded light as a further portion of the twice expanded light in a fifth direction via the emission surface, wherein the fifth direction at least partly does not extend in the spectacle lens, and wherein the third expansion element is set up to effectively focus the further portion of the twice expanded light.

Such an arrangement can ensure that the active ocular implant is reliably supplied with power over a greater range of lines of sight of the user.

In this case, the fourth direction may be opposite to the second direction. The fifth direction can correspond to the third direction or not be perpendicular to the third direction.

The fourth and the second direction might substantially correspond to one another. By way of example, the first expansion element may extend along the first direction and be configured such that the second and third expansion element each are at a distance from the first expansion element in the second direction with a spacing in the first direction. By way of example, the first expansion element can have an elongate embodiment in an upper region of a spectacle lens and the second and third expansion element may each be arranged below the first expansion element, wherein the second and third expansion element may be spaced apart from one another.

The twice expanded light may comprise a convergent light beam with a focal point.

The focal point can be at a distance of between 3 mm and 50 mm from the spectacle lens. Preferably, the focal point can be at a distance of between 10 mm and 30 mm from the spectacle lens.

Consequently, the focal point can be located in such a way that the focal point is located approximately at the center of rotation of the eye, for example less than 5 mm away from the center of rotation of the eye, for example in cases where the distance between the pupil and the spectacle lens is chosen in a range of approximately 10 mm to 20 mm and the distance of the pupil from the center of the eye, which may substantially correspond to the center of rotation of the eye, is approximately 9 mm. The focal point can also be located such that it is located approximately on the pupil of the eye, for example less than 5 mm away from the center of the pupil. The focal point can also be located between the center of rotation of the eye and the center of the pupil, for example less than 10 mm away from an imaginary connecting line, for example less than 5 mm away from an imaginary connecting line.

These values can be adapted accordingly in cases with different anatomical and/or device-related conditions.

In the case of the focus at the center of the pupil, this may be advantageous in that as much of the light as possible is coupled into the eye independently of a size of the pupil. If the focal point is placed close to the center of rotation of the eye, a uniform illumination can be ensured for different lines of sight if the area of the second expansion element is large enough. A compromise between the two described cases can be chosen if the focus is positioned along the connecting line.

The device may comprise a controller, wherein the controller may be set up to determine a line of sight of the user. Further, the device can be set up to adapt to the effective focusing of the twice expanded light in response to a change in the line of sight of the eye.

In the embodiments where a second and a third expansion element are available, the controller can also be set up to modify a ratio of the portions of the expanded light respectively guided to the second and the third expansion element in response to an identified line of sight. This can improve the energy efficiency of the device.

The device may comprise a recording device and a scanning mirror. In this case, the controller can be set up to determine the line of sight of the user on the basis of information from the recording device and to control the scanning mirror on the basis of the line of sight.

The device can be set up to increase the effective focusing in a sixth direction, wherein the sixth direction may be perpendicular to the third direction.

Increasing the focusing is understood to mean that the spatial extent of the light is increased in the focal plane in at least one direction, i.e., the light assumes a larger area in the focal plane. This may lead to the power density of the light with increased focusing being reduced in relation to the non-increased focusing for a fixed amount of light energy in the focal plane. Expressed differently, the brilliance of the light in the focal plane can be reduced. This can lead to improved safety of the device since it is possible to prevent light radiation that is too concentrated from being emitted by the device. This can ensure that safety-relevant limits of the irradiance for the individual regions of the human eye by the light source are undershot, both for the output coupled light and for beam expander elements.

Effective focusing can also be understood to mean the possibility of defining one or more beam waists. An increase of the focusing then is an anisotropic change in the shape of the beam waist for at least one beam waist, wherein, in a cross-section of the beam waist, for example along the third direction, the extent of the beam waist is increased in at least one direction, for example along the sixth direction which may lie in the cross-sectional plane and which may consequently be perpendicular to the third direction.

To increase the focus, the device may comprise a diffusing plate and/or a microoptical unit between the light source and a collimation optical unit, wherein the diffusing plate and/or microoptical unit is set up to generate a plurality of beams with a respective offset from one another and provide said light beams as the collimated light, and/or the light source comprises an active illumination optical unit which is set up to provide temporally changeable beams with a respective offset from one another as the collimated light, and/or the second expansion element and/or the emission surface is set up to scatter the twice expanded light, and/or the second expansion element and/or the emission surface is set up to generate a plurality of foci offset along the fourth direction.

These means for increasing the focus are examples of how the effective focusing of the second expansion element can be influenced.

A scattering functionality can also be brought about directly by the optical element itself in the case of some optical elements. By way of example, the second expansion element can comprise a scattering function, for example if the second expansion element is embodied as a volume hologram. A diffusing plate can additionally be used in such cases in order to obtain a combined effect. The diffusing plate can be dispensed with in other cases.

The twice expanded light can comprise a plurality of spatially restricted waves. These can respectively propagate at least partially in the third direction from different regions of the emission surface, wherein the plurality of spatially restricted plane waves at least partly cross and/or diverge.

Partly crossing can also mean that crossing only occurs in a projection of the spatially restricted plane waves onto a plane, for example by virtue of the waves not crossing in three-dimensional space on account of having a height offset. Expressed differently, there may be at least one plane that is spanned by two vectors, wherein one vector is a vector along the third direction such that the plane waves, projected into this plane, cross one another.

The second expansion element can have a plurality of segments and the plurality of segments can each be set up to provide a respective one of the plurality of spatially restricted waves.

By way of example, the plurality of segments can be hexagonal or rectangular or a combination thereof.

The first and/or second expansion element can comprise a multiply exposed volume hologram (sometimes also referred to as "multiplexed" volume hologram).

The plurality of spatially restricted waves can be at least one or a combination of:
plane waves, wavefronts with a convergent wavefront, wavefronts with a divergent wavefront.

In this case, a combination of spatially restricted waves is understood to mean that different wave types can emanate from different initial points. By way of example, a plane wave can emanate from a first position, a convergent wavefront can emanate from a second position and a divergent wavefront can emanate from a third position.

In some embodiments, at least one of the spatially restricted waves can substantially correspond to a second spatially restricted wave but have a spatial offset along the second and/or first direction.

Substantially correspond can mean that the propagation properties are similar or identical. By way of example, the propagation direction can substantially correspond; by way of example, respective normalized vectors along the propagation direction may include an angle of less than 10°, 5°, 1° or 0.1° with respect to one another. In this case, the initial points of the respective spatially restricted waves may be identical or differ.

The light source may comprise a laser diode with astigmatism and the spectacle lens may be set up to undertaken anisotropic divergence adjustment of the light from the laser diode.

The spectacle lens may be set up in different ways in order to undertake the anisotropic divergence adjustment of the light from the laser diode. By way of example, the divergence adjustment can be implemented by elements applied to the spectacle lens. By way of example, such applied elements can be refractive and/or reflective and/or diffractive surfaces, for example lenses, mirrors and/or surface gratings. In addition or as an alternative thereto, it may also be possible to use embedded elements, for example volume holograms as described above.

It is also possible to use a plurality of light sources by virtue of combining the concepts described herein with segmentation approaches. Such segmentations are known in their own right from WO 2017/180403 A1.

In this case, it may likewise be possible to introduce various light source-specific beam expanders, in each case as described above and below, into the spectacle lens. In this case, the expansion elements can be illuminated from different directions, for example. The beam separation required to this end either can already be implemented at an input coupling element, which may be embodied by means of two deflection elements for example, or can be implemented at a deflection element. It is possible as a result to illuminate a larger region of the retina for a given area of the spectacle lens and/or ensure power supply for a greater eye rolling range.

To achieve the anisotropic divergence adjustment of the light from the laser diode, the spectacle lens may comprise an input coupling element with anisotropic optical properties. However, the spectacle lens may also have anisotropic properties that are distributed over a relatively large spatial region; by way of example, the spectacle lens may comprise an optical waveguide with anisotropic properties, as a result of which the anisotropic divergence adjustment can be achieved.

The spectacle lens may comprise a waveguide and a transparent material, wherein the beam expander is arranged in or on the waveguide and the light from the light source is input coupled into the waveguide, wherein the transparent material at least partly surrounds the waveguide on at least one side.

Should the planar waveguide be manufactured from glass, but also in other cases, it may be advantageous from the safety point of view, for example for protection from splinters, to encapsulate the waveguide, for example between polymer layers which may comprise or consist of polycarbonate, for example. In addition to an encapsulation between two planar polymer wafers, the introduction into curved polymer glass is also conceivable, for example. This can significantly improve the aesthetics of the pair of spectacles. Very different manufacturing methods are available for both variants. Examples include:

fastening between two injection-molded shelves with an air gap. In this case, the total-internal reflection in the waveguide is against air, leading to smaller total-internal reflection angles in the glass. In this context, disadvantages in some examples may be additional reflections at the interfaces (ghost images, additional reflections).

By way of example, another option relates to bonding under the exclusion of air. In this case, total-internal reflection may occur at the adhesive, which may lead to larger total-internal reflection angles. This may have fewer reflections and/or ghost images as a consequence. In this case, use can be made of adhesives with a low refractive index, for example in the vicinity of n=1.33, but the use of other adhesives is also possible.

A further option relates to molding in a polymer. By way of example, the polymer can be UV curing. Molding can be carried out in different ways, for example between curved molds. In this case, it may be advantageous to use a waveguide with a high refractive index and large total-internal reflection angles. Decoupling can be performed in some embodiments by virtue of a planar waveguide initially being provided with a transparent layer with a low refractive index, for example a cured corresponding adhesive.

The transparent material can have a curved part on a side of the second expansion element that faces the eye of the user, wherein the transparent material is set up to modify the effective focusing of the light by refraction.

Consequently, a refractive error correction for the vision through the pair of spectacles may be possible, for example by the use of appropriate spherical or aspherical shapes on the side facing away from the eye and/or on the side facing the eye. At the same time, the additional curvature on the side of the spectacle lens facing the eye must already be taken into account when designing the beam expander. By way of example, this can be implemented by adjusting the second expansion element, for example by virtue of choosing a higher refractive power and/or a greater curvature of the provided wavefront by changing the properties of the second expansion element. This may lead to a scattering effect of a waveguide being able to be at least partly compensated.

The device can be set up to position the spectacle lens with a face form angle and an "as-worn" pantoscopic angle in relation to a straight line of sight of the user.

An "as-worn" pantoscopic angle or pantoscopic angle is understood to mean the angle in the vertical plane between the normal with respect to the front surface of a spectacle lens at the center thereof according to the boxed system and the fixation line of the eye in the primary position, which is usually assumed as horizontal.

A face form angle is understood to mean an angle between the plane of the spectacle front and the plane of the right lens shape, or of the left lens shape. The face form angle is sometimes also referred to as wrap angle.

The spectacle lens can comprise an input coupling element and an optical waveguide connected thereto, wherein the optical waveguide is set up to transmit the light to the first expansion element.

The light source of certain embodiments may comprise at least one of the following elements:

two individual light sources which are set up to provide light in different directions and/or in different wavelength ranges and/or at different illumination positions of at least one input coupling element for input coupling the light into the spectacle lens, a beam splitter, a scanning mirror, a switchable element.

In this way it is possible to switch between different light distributions of the light, for example a light distribution for supplying power to the ocular implant and a light distribution for other purposes, or two different light distributions for supplying power to the ocular implant by virtue of the individual light sources, the beam splitter, the scanning mirror and/or the switchable element being driven accordingly.

Preferably, the switchover in this case is implemented on the basis of a line of sight of the eye, which is captured by an eye tracker for example. Thus, power can be efficiently supplied to the ocular implant in the respective line of sight. In this way, the ocular implant can also be supplied over a large field of view.

The spectacle lens may have a cutout. This can facilitate some examinations of the eye when the pair of spectacles are worn.

According to a second aspect of certain embodiments, a method is provided for producing a user-specific pair of spectacles, wherein the method comprises:
  receiving head geometry information relating to the user,
  producing an device as claimed in any one of the preceding claims on the basis of the head geometry information.

In this case, head geometry information may comprise or be information in respect of the spatial arrangement of anatomical features, for example the relative position of the eye, the relative position of support points for a pair of spectacles, etc., as are known in their own right from EP 3 410 178 A1, for example.

The device can be an device as described above, in which the spectacle lens comprises an input coupling element and an optical waveguide connected thereto, wherein the optical waveguide is set up to transmit the light to the first expansion element.

The method can further comprise an activation of a portion of the spectacle lens in order to provide the above-described input coupling element and/or another input coupling element.

Such an activation is a user-specific definition of size and/or properties of the input coupling element.

By way of example, such methods can be applied when optically effective elements, for example diffractive elements, for example volume holograms, are generated within the scope of the method. By way of example, it may be possible by means of exposure to locally generate diffractive elements in a spectacle lens provided to this end. Such an exposure can be carried out by means of various processes, for example by means of laser writing, but other exposure methods are also possible.

Such an activation can be implemented on the basis of the head geometry information.

As mentioned above, input coupling elements generated by such an activation might be volume holograms, for example. To this end, the spectacle lenses may have a layer structure which is suitable for being activated and which extends over a bandwidth of possible positions for the input coupling element. The activation may comprise an exposure in such examples.

This allows a user-specific adaptation of mass-producible spectacle lenses, which can be produced for a multiplicity of users, to be undertaken.

The method can further comprise:
  determining a user-specific lateral offset for the input coupling element on the spectacle lens and/or
  the input coupling element being able to comprise an input coupling prism and the method being able to comprise adapting the position of the input coupling prism and/or
  at least two elements of the group of input coupling elements, the first expansion element and the second expansion element being able to be applied to at least two different wafers, and the method can further comprise:
  bonding the two different wafers to one another in a relative position with respect to one another, wherein the relative position is determined on the basis of the head geometry information.

The input coupling element can comprise a surface grating and/or a volume hologram, wherein the input coupling element is set up for a parameter range of head geometry information and has an input coupling surface that is larger than a light source input coupling surface of the light source on the input coupling element.

The method can comprise a positioning of the light source on the basis of the head geometry information, as a result of which the light source input coupling surface is fixedly arranged in relation to the input coupling surface.

In some embodiments, the method further comprises:
  deactivating a portion of the input coupling surface, wherein the deactivation is implemented by one or more of the following steps:
    electrically influencing an electrical grating in the input coupling surface,
    ablating a UV resist in a region of the input coupling surface,
    locally introducing a material into a surface grating, wherein the material has a similar refractive index to the material of the input coupling element,
    destroying an effect of some of a hologram by means of radiation, in particular electromagnetic radiation and/or temperature.

In this case, the UV resist can be designed by way of appropriate exposure and development such that the UV resist has diffractive elements, for example grating structures, for example volume holograms. Such diffractive elements can then be spatially selectively deactivated by local ablation but other types of deactivation are also possible, as described above and below.

Thus, for example, diffractive structures, for example holograms, for example volume holograms, can be locally deactivated by means of radiation such that the effect is locally destroyed. As an alternative or in addition thereto, a deactivation can also be implemented by means of an introduction of heat, for example by local, in some examples temporally restricted, change in the temperature of the diffractive structures.

In addition or as an alternative thereto, the method can also be combined with the above-described methods. By way of example, a first region of the spectacle lens, as described above, can be activated and a second region of the spectacle lens can be deactivated.

The entire spectacle lens or a portion of the spectacle lens can be activated as an input coupling surface. In this case, the portion can be chosen in such a way that a suitable position of an input coupling element in each case falls in the portion for a large bandwidth of user-specific head geometry information items. A spectacle lens with an activated portion can also be chosen as initial material for the method. In this case, the step of activation can be dispensed with in the method and/or can be brought forward into the production process for the spectacle lens. This may be advantageous in that the spectacle lenses can be produced cost-effectively, for example by virtue of layer structures being applied onto a region of the spectacle lens during the production, said region being larger than required for an input coupling surface in the case of the respectively adjusted spectacle lenses.

The input coupling element can now be provided in user-specific fashion by virtue of the second region, which may be a subset of the first region, being deactivated. The remaining part of the first region remains activated in such cases and can be used, in part or in full, as input coupling element.

Expressed differently, the input coupling element can be provided in individualized fashion by way of an activation process and/or can be provided by a selective deactivation of an active region, in a manner comparable to a positive and negative process. A combination of such processes is also possible, for example in different regions in which a first part of an input coupling element is provided by a positive process and a second part of an input coupling element is provided by a negative process.

The deactivation can consist in, or comprise the process of, deactivating a part of the input coupling surface, as described above. This may be advantageous in that an adjustment of the device to individual requirements and head geometries of a user can be very much simplified, for example by virtue of providing the same initial shapes for user groups and undertaking an adjustment of the devices to the individual using the aforementioned methods.

It may also be possible for such adjustments not to be undertaken by adjusting an individual element of the device but by a combination of different elements, i.e., for example, by modifying the first expansion element and the position of the light source. However, other combinations are also possible.

A first and a second material have a similar refractive index if the respective refractive indices of the first and the second material differ by less than 50%, less than 20%, less than 10%, less than 1%, for example.

A combination of activation and deactivation can offer the advantage of being able to reduce the costs for the production in this context.

The method according to certain embodiments can further comprise:
receiving required visual aid properties for the user,
adjusting the effective focusing of the device on the basis of the required visual aid properties.

In the examples where the device has a curved part, the effective focusing of the device can be achieved by virtue of, for example, the curvature being chosen on the basis of the required visual aid properties and the properties of the pupil replication system being adjusted on the basis of the curvature. As a result, it may be possible to optimize the beam guidance of the light largely independently of the light refraction properties of the device in a visible wavelength range.

As a result of the described methods it is possible to provide an device that is adapted to the individual requirements of a user, said device being able to offer improved comfort of wear and improved aesthetics.

The aforementioned features and those yet to be explained below can be used not only in the respectively specified combination but also in other combinations or on their own, without departing from the scope of the present invention.

BRIEF DESCRIPTION OF THE DRAWINGS

Below, the invention will be explained in detail by way of embodiments, with reference being made to the attached drawing. In the drawings.

DETAILED DESCRIPTION

Various embodiments are explained in detail below. These embodiments are only illustrative and should not be construed as restrictive. For example, a description of an embodiment with a multiplicity of elements or components should not be construed as meaning that all of these elements or components are necessary for implementation. Rather, other embodiments also may contain alternative elements or components, fewer elements or components or else additional elements or components. Elements or components of different embodiments can be combined with one another, unless stated otherwise. Modifications and variations which are described for one of the embodiments can also be applicable to other embodiments.

In order to avoid repetition, the same elements or corresponding elements in various figures are denoted by the same reference sign and are not explained a number of times.

The figures are geared towards illustrating the underlying principles. Surface shapes and refractions, for example, may therefore be indicated schematically. By way of example, refractions may be illustrated in exaggerated fashion or may be neglected.

A retinal implant is used in the following embodiments as an example of an active ocular implant. However, the techniques described are also applicable to other active ocular implants, for example the ocular implants mentioned at the outset.

Figure 1:
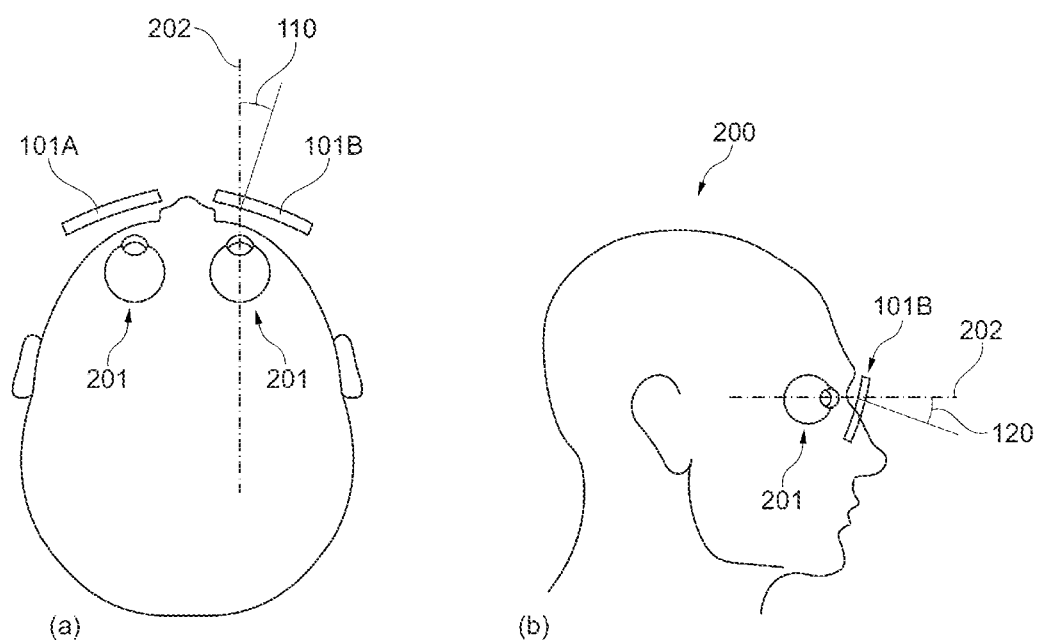
FIG. 1 shows a diagram for elucidating angles of a spectacle lens when the latter is worn by a user.

FIG. 1 shows a sketch for elucidating angles of a spectacle lens when the latter is worn by a user.

An device for supplying power to an active ocular implant in an eye 201 of a user 200 can be embodied as a head-worn, spectacle-like system and can comprise at least one spectacle lens. In the shown example of FIG. 1 the device comprises two spectacle lenses 101A, 101B. FIG. 1(*a*) shows a plan view while FIG. 1(*b*) shows a side view of a user 200 of the device. The spectacle lenses 101A, 101B may have different angles relative to the straight line of sight 202 of the user 200. As shown in FIG. 1, the device can be embodied such that a face form angle 110 and an "as-worn" pantoscopic angle 120, as described above, arise. The "as-worn" pantoscopic angle 120 can be between 5° and 20°, for example, and the face form angle 110 can lie between 5° and 20°, for example. Such angles not equal to 0° may be advantageous for the device from an aesthetic point of view.

Figure 2:
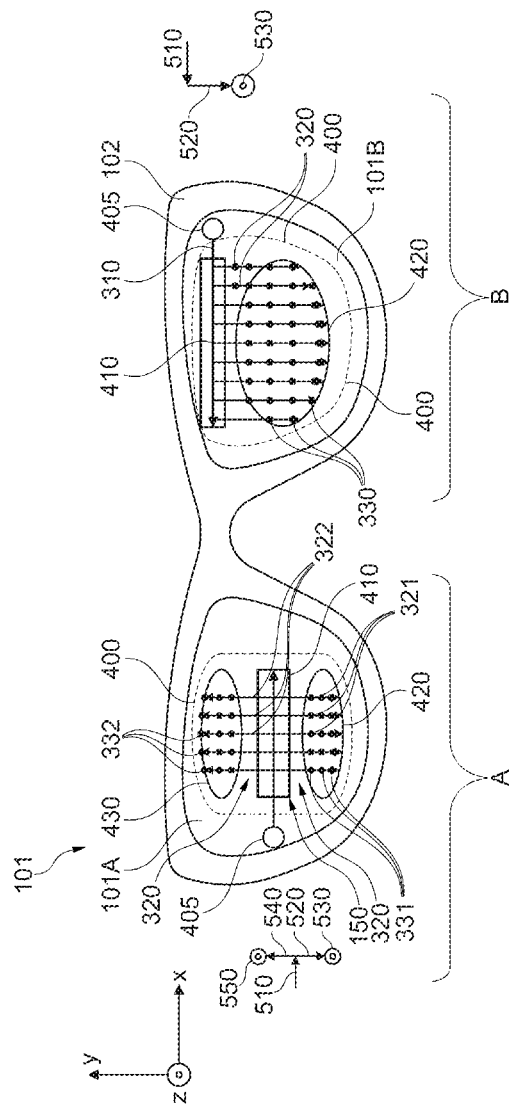
FIG. 2 shows a pair of spectacles with different embodiments for the left and right spectacle lens.

FIG. 2 shows an embodiment of an device for supplying power to an active ocular implant in an eye of a user. In this embodiment, the device is embodied as a pair of spectacles 101 which comprises two spectacle lenses 101A and 101B which are arranged in a frame 102. The device of the embodiment in FIG. 2 in each case comprises an device A for supplying power to an active ocular implant in the left eye and an device B for supplying power to an active ocular implant in the right eye. It should be noted in this case that further embodiments may also comprise only one of the two devices A and B, for example be embodied as a monocle or possibly comprise one device, for example device A, and be embodied as a regular pair of spectacles such that the spectacle lens 101B of this example would then not comprise a beam expander, for example if an active ocular implant is only present in one eye of the user.

In the example shown, the pair of spectacles 101 provides the power supply for both an active ocular implant in the left eye and an active ocular implant in the right eye. In such cases where the pair of spectacles 101 provides devices A, B for both eyes, the devices for the left eye A and for the right eye B can be identical or similar, for example mirror symmetric. However, they may also have different embodiments, as shown in the example of FIG. 2. In the shown example of the device 100, the device comprises an device A for the left eye from the view of the patient and a second device B for the right eye from the view of the patient. In this case, the spectacle lenses 101A, 101B of the devices A, B can be at an angle to the straight line of sight, as already explained in conjunction with FIG. 1.

The device B shows a first embodiment of an device with a spectacle lens 101B for supplying power to an active ocular implant in a right eye of a user. The device comprises a light source (not shown), wherein light from the light source is provided at an input coupling element 405. It should be observed in this context that an input coupling element 405 is not present in some embodiments but that a light source can be directly worked into this position. It is also possible that one or more light sources are situated in the frame 102.

The device comprises a beam expander 400, which is arranged in the spectacle lens 101 in the example of FIG. 4. The beam expander 400 comprises a first expansion element 410 and a second expansion element 420.

The device B is set up to input couple light 310 from the light source into the spectacle lens 101 and guide said light to the first expansion element 410. The first expansion element 410 is set up to receive the light 310, expand said light along a first direction 510 and guide said light as expanded light 320 to the second expansion element 420 in a second direction 520.

This may offer the advantage of the design degrees of freedom during the creation of such pupil expansion elements allowing the illumination profiles of the device to be adjusted to the requirements of the power reception devices of the active ocular implants.

Depending on the type of the active ocular implant, for example a homogenous illumination pattern or any other intensity distribution pattern adjusted to the receiver geometry and requirements may be desirable and may be provided by pupil expansion systems.

What should be observed in this context in the illustration of FIG. 2 is that the respective directions for embodiments A and B are chosen to be different (mirror symmetric in the example shown). From this, it is evident that the specific directions should only be understood as exemplary. By way of example, if the input coupling element 405 of device B were attached bottom left instead of the shown position top right, the directions would reverse accordingly so that the same expansion effect can be obtained.

The second direction 520 can differ from the first direction 510; this difference is 90° in the shown example of device B.

The second expansion element 420 is set up to receive the expanded light 320, expand said expanded light along the second direction 520 and provide said expanded light as twice expanded light 330 in a third direction 530 via an emission surface 440, wherein the third direction 530 at least partly does not extend in the spectacle lens 101. In the shown examples of devices A and B in FIG. 2, the third direction 520 generally extends from the plane of the drawing toward the observer such that the light 530 is guided to the respective eye of the user in each of devices A and B. The example of FIG. 2 illustrates discrete output coupling points for respective light beams; however, it may also be possible for continuous output coupling to extend along the surface or a combination of regions in which there is planar and discrete output coupling, or in which the component of the output coupled light in comparison with the component of the transmitted light varies locally. In particular, this can attain a uniform surface light intensity. However, deliberately non-uniform illumination profiles can be brought about in other embodiments, for example in order to be able to meet certain requirements of an active ocular implant.

The second expansion element 530 is set up to effectively focus the twice expanded light 330. This is explained in more detail in the context of FIGS. 3A, 3B to 5.

The device A shows another example. Device A is based on device B, with the same reference signs denoting the same elements. However, the respective properties and directions 510-530 can deviate from the embodiment of device B.

Additionally, in relation to the beam expander 400 of device B described above, the beam expander 400 of device A comprises a third expansion element 430.

In device B, the expansion element 410 is set up to provide the expanded light in the second direction 520, as explained above. The expansion element 410 of device A is set up to expand and split the light. The expansion element 410 provides a portion of the expanded light 320 in the second direction 520. The first expansion element 410 of device A guides a further portion of the expanded light 320 to the third expansion element 430 in a fourth direction 540. In this case, the fourth direction differs from the first, second and third direction. In the shown example, the fourth direction 540 is opposite to the third direction 530.

The third expansion element 430 is set up to receive the expanded light 320 or the further portion of the expanded light 322, expand said expanded light along the fourth direction 540 and provide said expanded light as a further portion of the twice expanded light in a fifth direction 550 via the emission surface 430, wherein the fifth direction 550 at least partly does not extend in the spectacle lens.

The twice expanded light 330 accordingly comprises a portion 331 and the further portion 332, wherein the portion 331 of the twice expanded light is the twice expanded light 330 provided by the second expansion element 420.

The third expansion element 430 is set up to effectively focus the further portion of the twice expanded light 332.

In the example of device A shown, the third direction 530 and the fifth direction 550 are identical. However, this need not necessarily be the case. By way of example, it may be possible that the fifth direction 550 has a directional component in the negative y-direction and the third direction has a directional component in the positive y-direction. As a result, it may be possible that the positioning of the third and fourth expansion element can also contribute to the effective focusing of the twice expanded light 331, 332, 330.

It may also be possible for the respective directions to represent centroid directions, i.e., for example describe a mean value of the directions with which light is output coupled from the expansion devices. As a result, it may be possible, for example, for the twice expanded light provided by the third expansion device 430 to be focused on a point. However, other beam paths of the twice expanded light are also possible. This will be explained further below on the basis of examples.

Figure 3A:
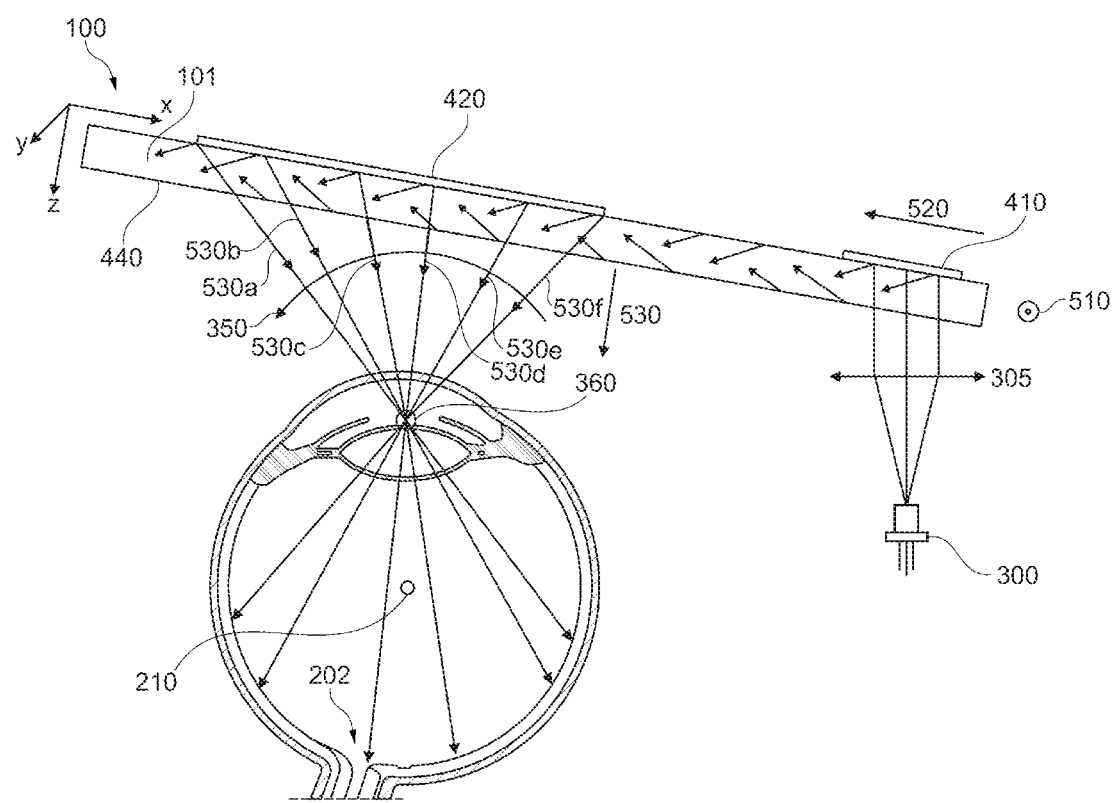
FIG. 3A and FIG. 3B show cross-sectional views of different embodiments with different effective focusing.
Figure 3B:
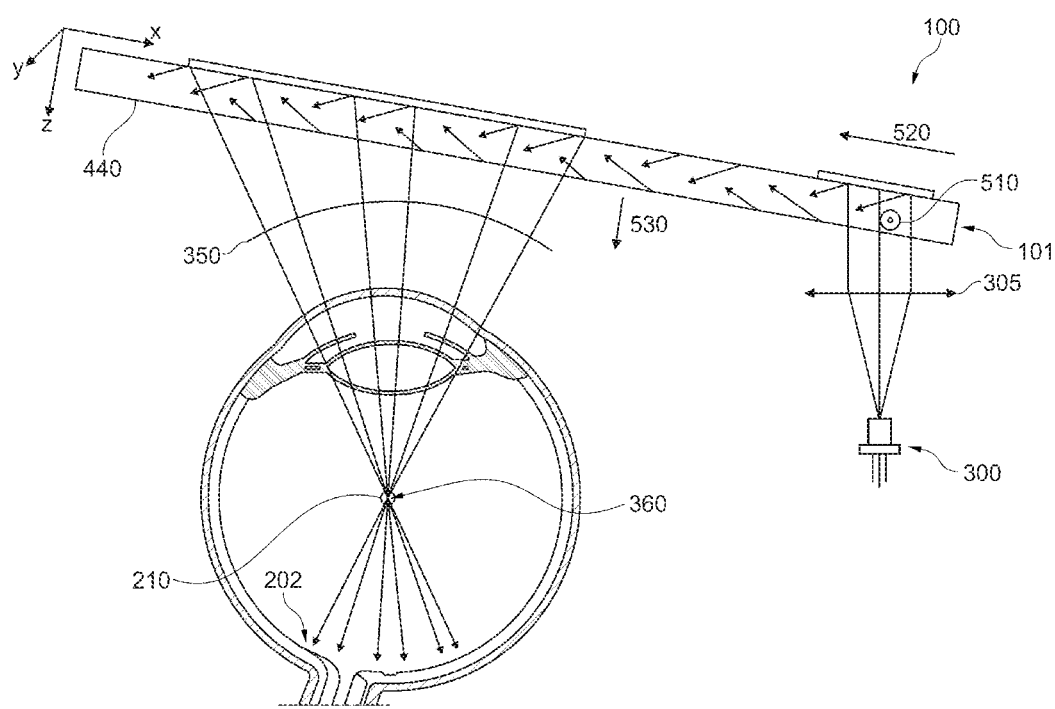

In this respect, FIGS. 3A and 3B as well as 4A and 4B show cross-sectional views of different embodiments with different effective focusing.

FIGS. 3A, 3B, 4A, 4B and 5 schematically show a light source 300 which may be an infrared light source for example. The device can further comprise one or more optical elements between the light source 300 and the input coupling element 405. The shown example schematically indicates a collimation optical unit 305 but a combination with other optical elements, for example the aforementioned diffusing plates, is also possible. Deflection units can also be provided such that the light propagates from an input coupling element (not shown) in the first direction 510 and is provided in the third direction 530 as twice expanded light by the first 410 and second 420 expansion element. FIGS. 3A, 3B, 4A and 4B show different variants of how the effective focusing mentioned can be achieved.

In this case, effective focusing is understood to mean steering the twice expanded light 330 to an imaginary focal surface 340 between the emission surface 440 and the active ocular implant 202 along the third direction 530, wherein the imaginary focal surface 340 is smaller than the emission surface 440.

Various examples to this end are shown in the figures. In FIG. 3A, the second expansion element generates a light distribution which is set such that the twice expanded light emitted by the emission surface 440 represents a convergent light beam, the focal point 360 of which is located in the pupil of the eye. It should be observed in this context that the directions described above and below represent effective directions. By way of example, the propagation is in the second direction 520 with however individual light beams being reflected along the spectacle lens by total-internal reflection and therefore, as indicated by the arrows, possibly propagating in different directions than the second direction 520 on small scales. The twice expanded light is also provided in the third direction 530, but individual light beams thereof may have different directions 530a-f to this end. The same applies accordingly to the other examples.

In some embodiments of FIG. 3A, the relative position of the focal point in the pupil may lead to the focus remaining static when the eye rotates and possibly missing the pupil in the case of extreme changes in the line of sight.

The device 100 of FIG. 3B substantially corresponds to the device 100 of FIG. 3A; however, a different focal point 360 is chosen here such that the focal point 360 is not located in the region of the pupil but in the region of the center of rotation of the eye 210. Consequently, the beam fans open again after propagation through the pupil of the eye and illuminates an extended area on the retina.

In the illustrated embodiments, this leads to the illumination being less strongly dependent on the line of sight of the user. An advantage in this case may be that a constant large area of the retina can be illuminated, even in the case of an eye rotation. However, in some embodiments this focal point 360 can lead to only some of the emitted light, which is provided as a convergent beam, reaching an active ocular implant 202 for a given line of sight, which may worsen the energy balance of the device 100.

Therefore, an alternative option consists of measuring the line of sight of the user, for example by means of eye tracking, and actively updating the focus of the convergent beam, for example by virtue of modifying the direction of the input coupled beam by means of a scanning mirror between the light source 300 and the spectacle lens 101.

Depending on the power needs of the active ocular implant, focusing on a point in some embodiments may lead to a high power density possibly occurring in the vicinity of the focus of the rays, said power density possibly exceeding the legal limits. To counteract this, the focus may be increased laterally, for example in a sixth direction 560. This can be achieved with an device as per FIG. 3A and FIG. 3B by introducing diffusing plates or microoptical units, as described above. By way of such optical elements it is possible to deflect respective foci to different lateral positions. In this case, the region of the foci can be illuminated homogenously or discretely.

A scattering functionality can also be brought about directly by the optical element itself in the case of some optical elements. By way of example, the second expansion element can comprise a scattering function, for example if the second expansion element is embodied as a volume hologram.

Another option will be described below in the context of FIG. 4A and FIG. 4B.

Figure 4A:
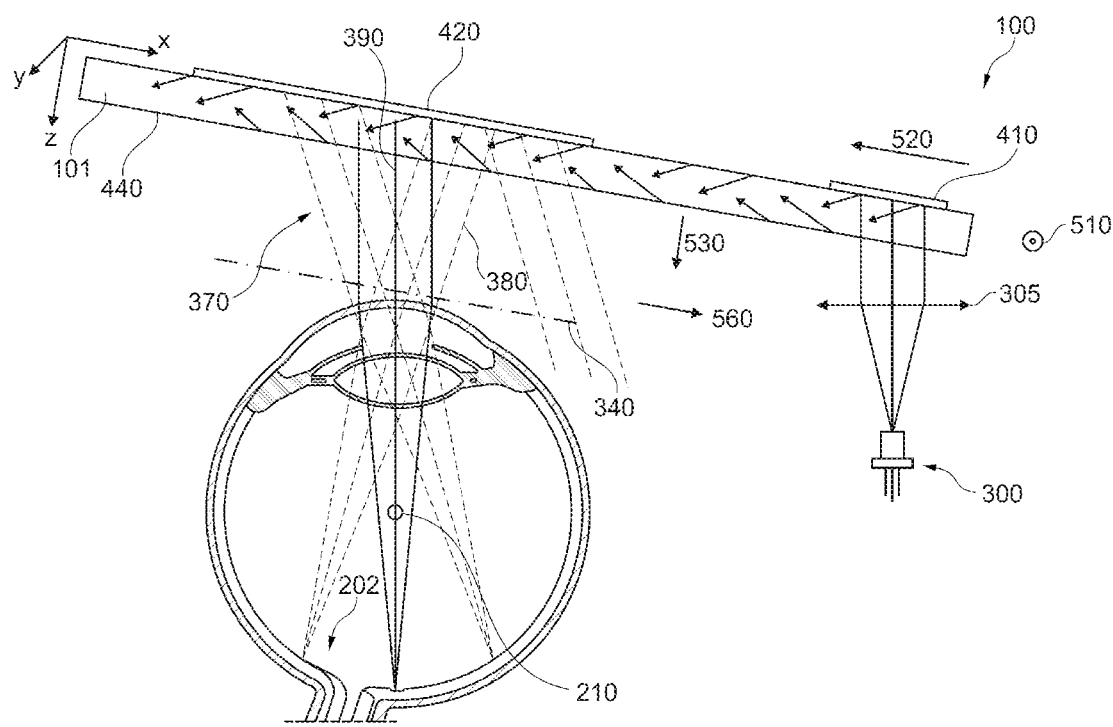
FIG. 4A and FIG. 4B show a further embodiment with alternative effective focusing via a plurality of spatially restricted waves.
Figure 4B:
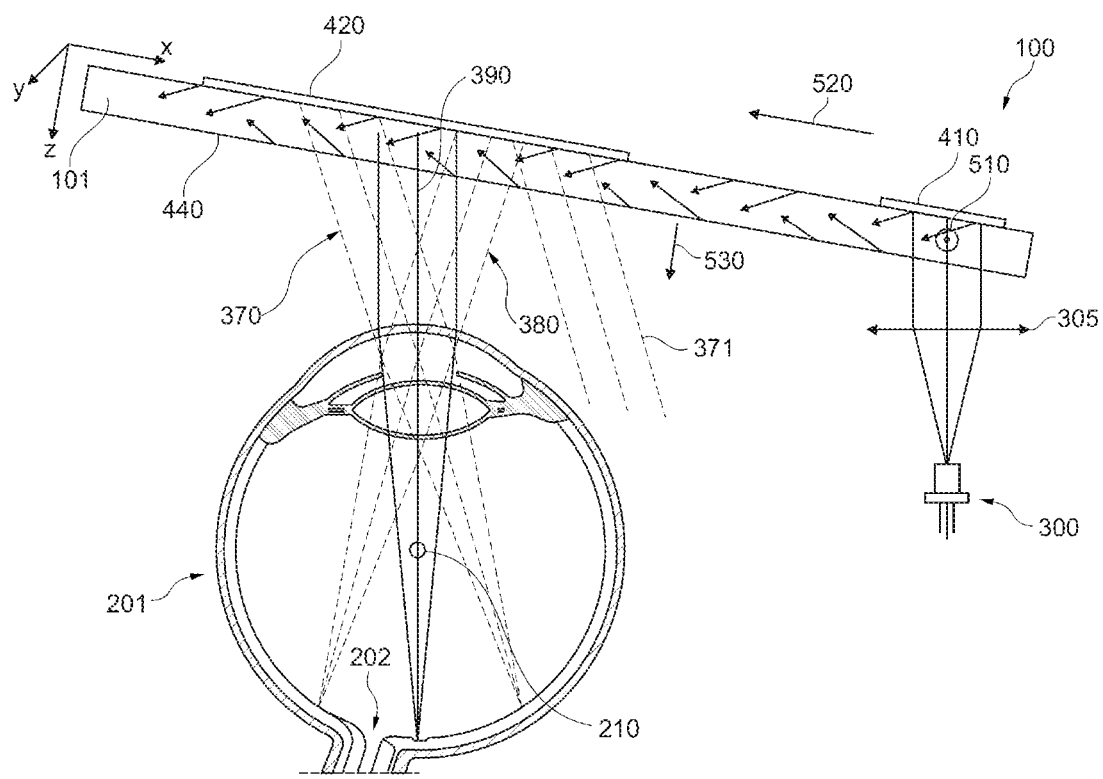

FIG. 4A and FIG. 4B show alternative effective focusing by means of a plurality of spatially restricted waves.

While the devices 100 in FIG. 3A and FIG. 3B provide convergent light beams 350 as twice expanded light, the device 100 in FIG. 4A and FIG. 4B is set up to achieve effective focusing of the twice expanded light by virtue of the twice expanded light 330 comprising a plurality of spatially restricted waves 370, 380, 390, which each, at least in part, propagate from different regions of the emission surface in the direction of the third direction 530, wherein the plurality of spatially restricted plane waves at least partly cross and/or diverge. Consequently, the effective focusing is achieved by the spatial arrangement of the plane waves.

The examples in FIG. 4A and FIG. 4B show plane waves but other waveforms are also possible, for example plane waves, wavefronts with a convergent wavefront or wavefronts with a divergent wavefront.

By way of example, this can be achieved by virtue of segmenting the output coupling element and introducing a hologram with different period and orientation in each segment. By way of example, the segments could be attached in a hexagonal or rectangular pattern. Manufacturing the output coupling element as multiply exposed (multiplexed) volume hologram is also conceivable. In the case of such multiply exposed volume holograms it is also possible for individual segmentation regions to spatially overlap in part or in full.

In such embodiments the individual plane waves are focused by the optical system of the eye and generate a point grid on the retina which can then supply power to the active ocular implant.

To avoid the beam power density on the retina exceeding the specified limits, it is possible to take additional measures to broaden the focal points. On the one hand, it is possible to use all previously discussed approaches for introducing a scattering function.

On the other hand, there is the option of output coupling a multiplicity of wavefronts with a residual divergence instead of plane waves. In this case, the individual wavefronts can be divergent or convergent. This shifts the focus of the partial waves in front of or behind the retina and the radiation power density drops. At the same time, this can lead to a more homogenous illumination of the retina.

In the example of FIG. 4B, the spatial distribution of the twice expanded light additionally has a spatial offset. In the example of FIG. 4B, this is shown in exemplary fashion with a spatial offset of the plane wave 370, which has an offset along the first direction and which repeats in the form of the plane wave 370. However, a repetition in the first direction 510 or by a combination of a first direction and second direction are also possible. The provision of plane waves with the same propagation direction by multiplexing at different positions of the spectacle lens 101 may be advantageous in that a power supply for the active ocular implant can be ensured even for significant rolling movements of the eye.

Figure 5:
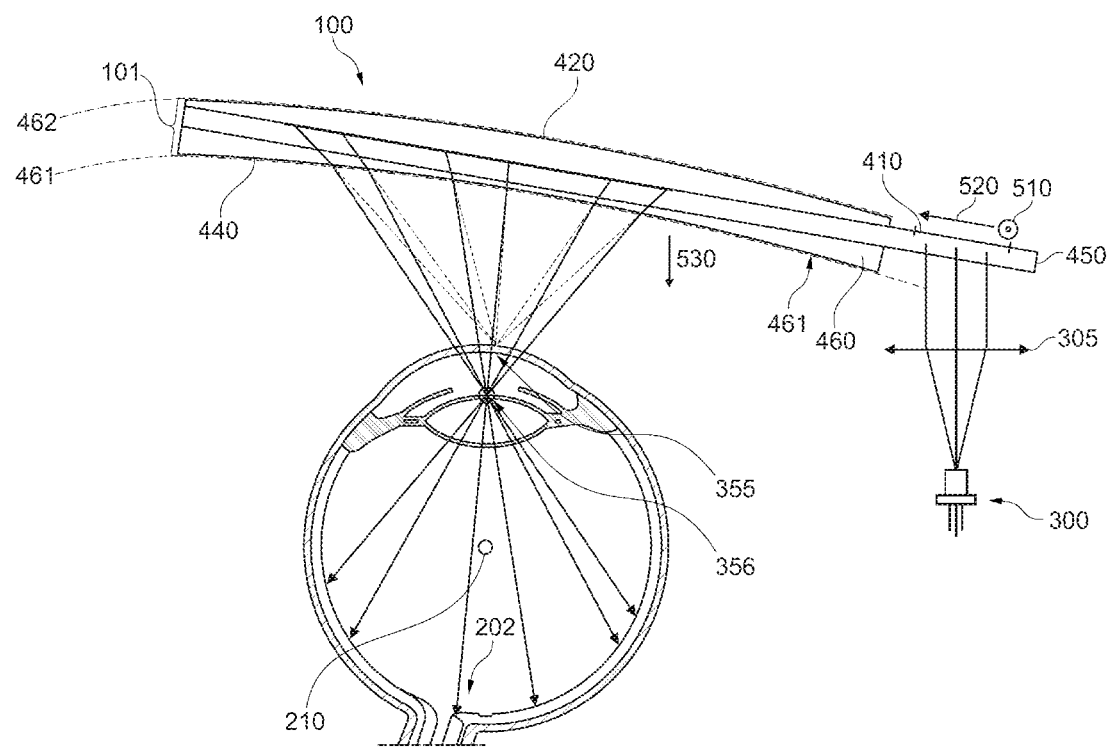
FIG. 5 shows a further embodiment with a waveguide that is surrounded by transparent material.

FIG. 5 shows a further embodiment with a waveguide that is surrounded by transparent material.

The spectacle lens 101 shown in FIG. 5 comprises a waveguide 450 and transparent material 460. The properties explained below in conjunction with FIG. 5 are explained in conjunction with a modified embodiment of FIG. 3A. However, a combination with other embodiments is also possible.

The beam expander 400 is arranged in the waveguide 450 and the light is input coupled from the light source 300 into the waveguide 450. In the example shown, the transparent material 460 surrounds the waveguide 450 on the side facing the eyes and the side facing away from the eyes. However, other embodiments are also possible.

In the example shown in FIG. 5, the waveguide 450 can be a planar waveguide made of glass. Then, the transparent material 460 can serve as protection against splinters, as described above. In the example shown, both the side of the transparent material facing away from the eyes and the side of the transparent material facing the eyes have a curved part 461, 462. As a result, the transparent material has refractive power. The curved parts here are only exemplary, other glass shapes known from spectacle optics can also be used, for example any combination of concave and convex lens shapes or more complex shapes, for example progressive addition lens shapes or lens shapes that can compensate an astigmatism.

If such a transparent material is present this should be taken into account in the optical design of the beam expander since the light is refracted at the interfaces between waveguide 450 and transparent material 460 and at the interface between transparent material 460 and air. In the example shown, the scattering effect of the inner curved part 461 is compensated by an increase in the curvature of the wavefront generated by the waveguide. Without this compensation, the focus would not, like in FIG. 3A, be located in the region of the pupil, as indicated by the dashed lines 355. The focal point is located back at the right position 356 as a result of these instances of refraction being taken into account.

Expansion elements like the above-described expansion elements can also form a tree structure. Such an device 1100 is illustrated in FIG. 7.

Figure 7:
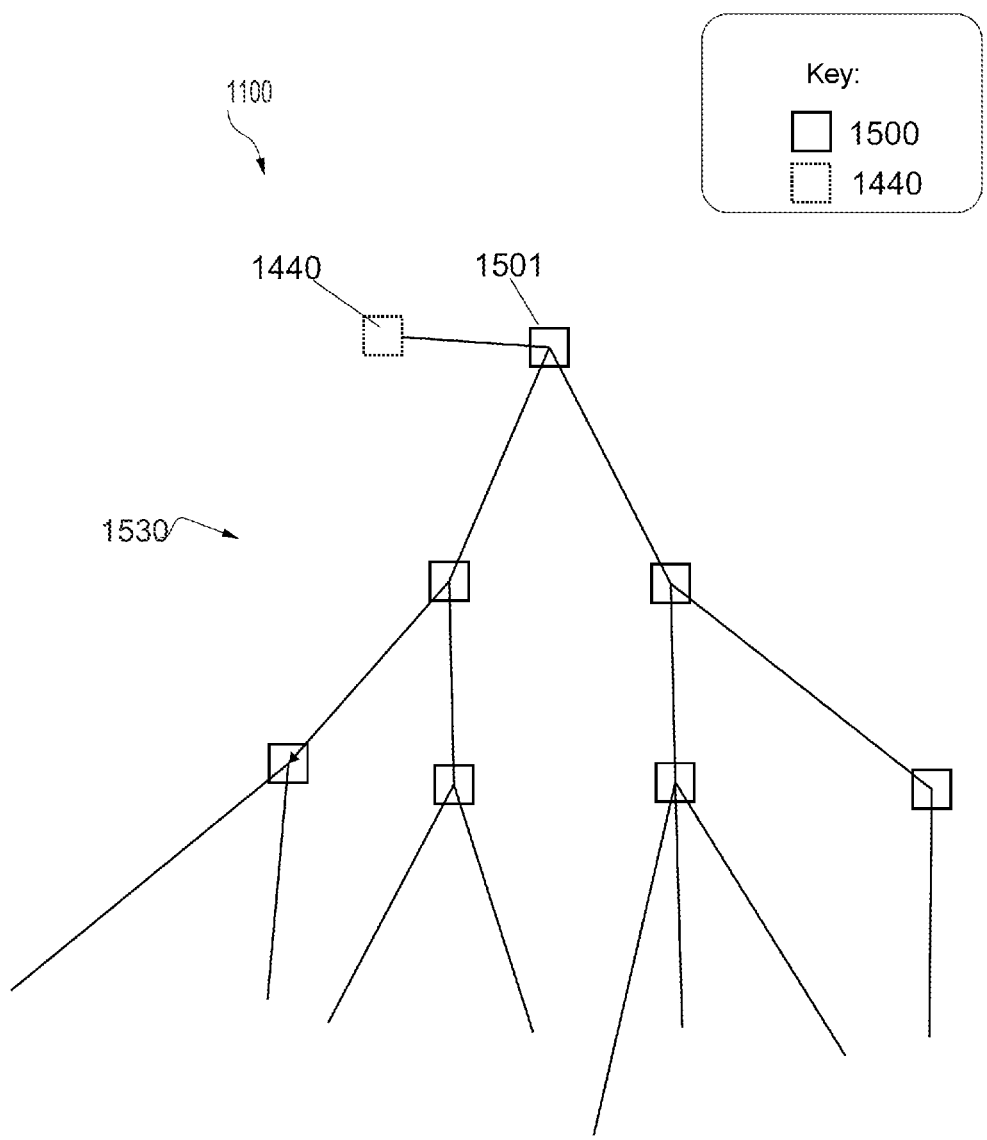
FIG. 7 is a diagram for elucidating a tree structure in some embodiments.

FIG. 7 in this case shows a detailed view of an device 1100 which, as described for some of the embodiments above, can be arranged in a spectacle lens that serves as an optical waveguide. A multiplicity of expansion elements 1500 are shown schematically, wherein a first expansion element receives light directly or indirectly (via other elements) from a light source 1440. The further elements of the multiplicity of expansion elements 1500 have a tree structure 1530.

In this case, the expansion elements 1500 can be set up both to transmit light in the spectacle lens to a next expansion element 1500 in the tree structure and to output couple light from the spectacle lens in order to steer light to an eye. As a result of the tree structure, the degree of freedom when designing a light distribution of the light that can be generated by the device 1100 is increased further.

Figure 8:
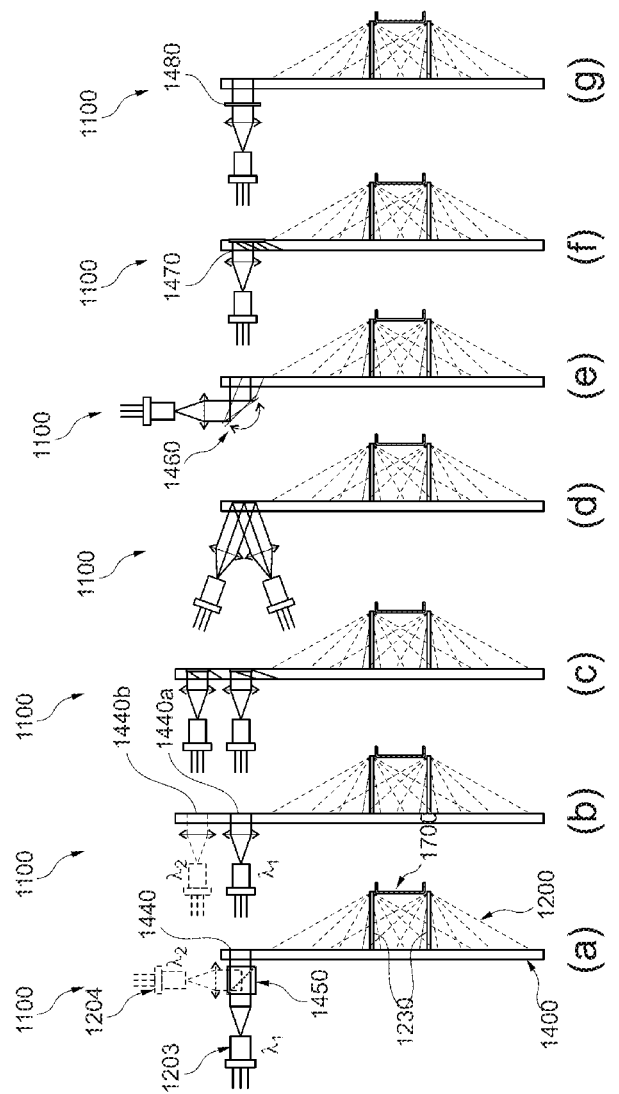
FIG. 8 shows devices according to various embodiments, which are multi-channel and/or switchable.

FIG. 8 shows devices according to various embodiments, which are multi-channel and/or switchable. To this end, light from two different light sources, for example, can be used. By way of example, light from one light source can serve to supply power to an ocular implant as described above while light from another light source serves other purposes, for example for illumination or for the projection of information. In other embodiments different wavelengths can be provided to supply ocular implants. In yet other embodiments, light with different light distributions can be provided to supply ocular implants. By way of example, a line of sight of the eye can be captured by means of an eye tracker and a light distribution can be selected on the basis of the line of sight in order to efficiently supply power to the ocular implant for the respective line of sight. By way of example, a line of sight to the eye can be monitored by a so-called eye tracker and the light distribution can be chosen on the basis of the line of sight in order to optimize a power supply for the implant and/or in order to ensure that the greatest possible portion of the emitted energy reaches the ocular implant.

In this way, the ocular implant can also be supplied over a large field of view.

In this case, the partial figures of FIG. 8(a) to FIG. 8(g) show different examples of multi-channel or switchable devices which are set up to provide different light distributions, for example for supplying power to an ocular implant.

Different concepts of multi-channel optical waveguide systems are described below on the basis of devices 1100 in (a) to (g). The concepts can make use of high spectral and/or angular selectivity of expansion elements, which are implemented as diffractive elements, for example with volume holograms or other microstructured optical elements, in order to be able to transmit a plurality of beams independently of one another within the same volume of a spectacle lens that serves as a light guide 1400. In this context, a high spectral selectivity is understood to mean the drop in efficiency of the element by for example 50% of the full width at half maximum (FWHM) in the case of wavelength deviations from the design wavelength of for example <40 nm, for example <10 nm.

A high angular selectivity is understood to mean a drop in the efficiency of the element by 50% of the FWHM in the case of a deviation of the ray angle of incidence from a design angle for which the respective optical element is designed, for example in order to receive an associated input light beam from this angle, of for example <10°, for example <2°. In such cases, but without being restricted thereto, a plurality of beams can propagate in different directions and/or with different wavelengths within the same volume of the optical waveguide 1400 and can be selectively coupled and transmitted by associated optical elements, which is sometimes also described as "fitting". Expressed differently, selectively acting expansion elements can be provided within an identical volume of the light guide 1400. In this case, expansion elements can be set up to receive at least one associated input light beam with an input beam profile and to provide a multiplicity of associated output light beams with respective output beam profiles, for example output couple one light beam from a spectacle lens and transmit another light beam in the spectacle lens. These expansion elements can operate in superposition and convert the light for different characteristics, for example angles of incidence, into different light distributions. Sometimes this is also described as multiplexing, for example spectral multiplexing, if the optical elements, for example volume holograms, are set up such that they have a different coupling behavior for different spectral properties of the light. Other types of multiplexing are also possible, for example angle- or polarization-dependent multiplexing, and combinations thereof.

This basic idea is briefly explained below using the example of side views of the device 1100 in FIG. 8. In this case, only a maximum of two light sources are shown in exemplary fashion even though this naturally should not be construed as restrictive; more complex systems with for example more than two light sources are also possible.

The device at (a) shows an device 1100 which is set up to receive light from a first light source 1203 at a first wavelength $\lambda 1$ and light at a second wavelength $\lambda 2$ from a second light source 1204, and to generate a light distribution 1200 for each wavelength received. In the example shown, the light distribution 1200 comprises a light distribution which is composed from the light distribution 1200, for example for supplying power to an ocular implant, and a light distribution of fixation markers 1230. Such a structure may be advantageous in that it is possible to provide various light distributions in different wavelength ranges for different purposes using the same optical waveguide 1400, for example the fixation markers 1230 at a wavelength $\lambda 2$ of the second light source 1204 in the visible range and infrared light at a wavelength $\lambda 1$ of the first light source 1203 in the infrared in the example shown. It is also possible for both light sources to transmit in the infrared at different wavelengths, in particular for generating different light distributions for supplying power to the ocular implant.

FIG. 8(b) shows an alternative implementation of the device of FIG. 8(a) with a differently designed input coupling element 1440. Input coupling elements described with reference to FIG. 8 can be realized with diffractive elements, in particular buried diffractive elements. In this embodiment, the input coupling element 1440 comprises two different regions, a first input coupling region 1440A being set up to input couple the light from the first light source 1203 and a second input coupling region 1440B being set up to input couple the light from the second light source 1204 into the optical waveguide 1400.

FIG. 8(c) to FIG. 8(g) show different options for realizing switchable systems and/or systems that facilitate a plurality of light distributions in overlaid fashion, which is sometimes also referred to as a superposition.

In the example of FIG. 8(c), the light sources 1203, 1204 are arranged with a lateral offset and are input coupled by input coupling elements 1440A, 1440B into the optical waveguide 4100 at different points.

In this case, the respective associated input coupling elements 1440A, 1440B can be configured in such a way that different types of input coupling into the optical waveguide 1400 are achieved, for example different input coupling angles, even in the case of light sources 1203, 1204 of the same kind. Consequently, the device 1100 can be set up to provide two light distributions, a respective light distribution per light source in the example shown. In some examples, these light distributions can be chosen independently of one another, for example on account of the above-described angle selectivity and/or wavelength selectivity of the utilized optical elements.

FIG. 8(d) shows a variation of FIG. 8(c), wherein the two light sources 1204, 1203 are incident on an input coupling element 1440 at different angles. The latter is set up to input couple the two light sources into the optical waveguide 1400 independently of one another. Only one light source 1203 is present in the example of FIG. 8(e). In this case, the angle of incidence of the light of the light source 1203 is varied by a scanning mirror 1460, as a result of which a switchable light distribution arises. A switchable optical element 1470, for example a switchable hologram, is present in the optical waveguide 1400 in the example of FIG. 8(f). This can also achieve a superposition of different light distributions. In the example of FIG. 8(g), a polarization-changing element 1480 changes the polarization properties of the light from the light source 1203. The optical elements of the device 1100 may have polarization-dependent properties such that different light distributions can also be brought about by varying the polarization of the light incident on the device 1100.

The examples shown in FIG. 8(a) to FIG. 8(g) can also be combined with one another. By way of example, different light sources with different polarization directions—corresponding to the example of FIG. 8(g)—can be combined with a scanning mirror—as shown in FIG. 8(e). However, any other combinations of the shown elements and procedures are also possible.

An opening in the spectacle lens may be desirable in some embodiments, for example in order to be able to carry out examinations of the eye. In order to nevertheless provide a suitable light distribution of light for supplying power to an ocular implant, such an device can be configured in that case as explained with reference to FIGS. 9A, 9B and 10.

Figure 9A:
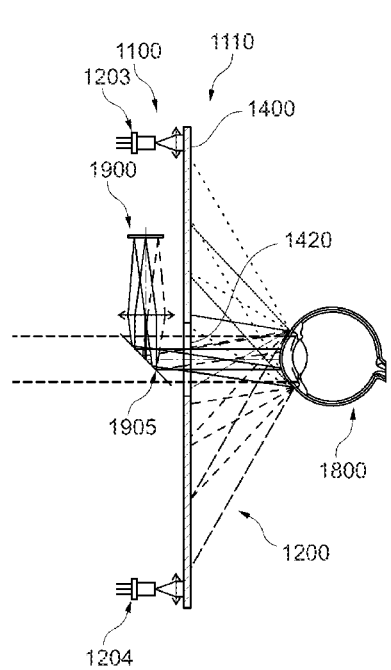
FIG. 9A shows a side view of a device which facilitates an examination modality.
Figure 9B:
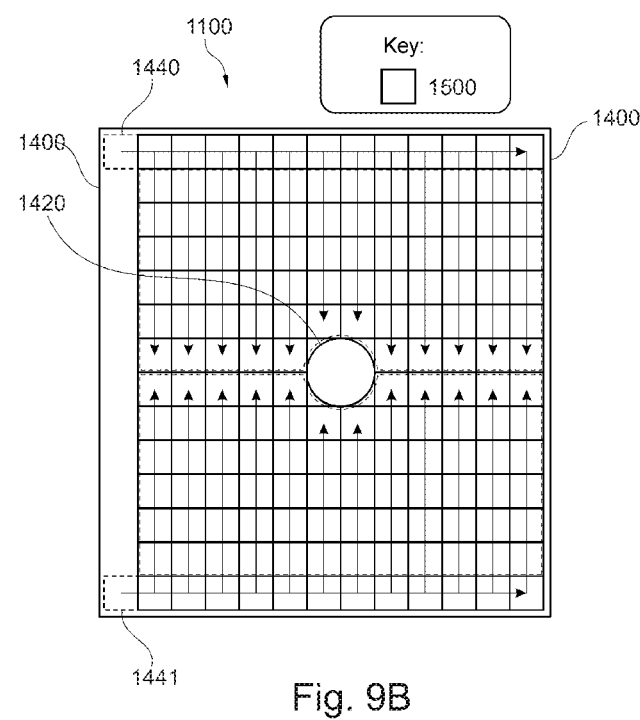
FIG. 9B shows a frontal view of the device of FIG. 9A.

FIG. 9A shows a lateral view of an device 1100 according to an embodiment. FIG. 9B shows a frontal view of the device 1100.

The device 1100 provides a light distribution 1200 for supplying power to an ocular implant of an eye 1800. Using a switchable device as explained with reference to FIG. 8, it is possible in some embodiments, in switchable fashion, to provide a light distribution for illuminating the eye for an examination, for example for keratometric measurement of the cornea of the eye 1800. Moreover, the eye can be examined through a cutout 1420 in a spectacle lens that serves as an optical waveguide 1400. By way of example, in the case of the aforementioned keratometric examination, the light reflected by the cornea of the eye 1800 is detected by a detection device 1900 along a detection beam path 1905 and said light can subsequently be analyzed in order to deduce the topology of the cornea. As mentioned, the optical waveguide 1400 of the device 1100 has the cutout 1420. In order to obtain a light distribution 1200 suitable for supplying power to an ocular implant or else possibly for illuminating purposes, for example for keratometry, despite the cutout 1420, said light distribution covering an entire visual field of the eye 1800 where possible or illuminating the entire eye to be examined, the light is provided by two light sources 1203, 1204 and input coupled by two input coupling elements 1440, 1441. Proceeding from the respective input coupling elements 1440, 1441, the light is replicated by way of a multiplicity of expansion elements as described above and output coupled as light distribution 1200 in the direction of the eye 1800.

In the example of the device shown, the surface normal of the optical waveguide 1400 is arranged in parallel with a principal visual axis of the eye 1800. However, in other embodiments, the normal of the optical waveguide can be arranged precisely not in parallel with the principal visual axis of the eye 1800. By way of example, this can reduce or avoid reflections.

Figure 10:
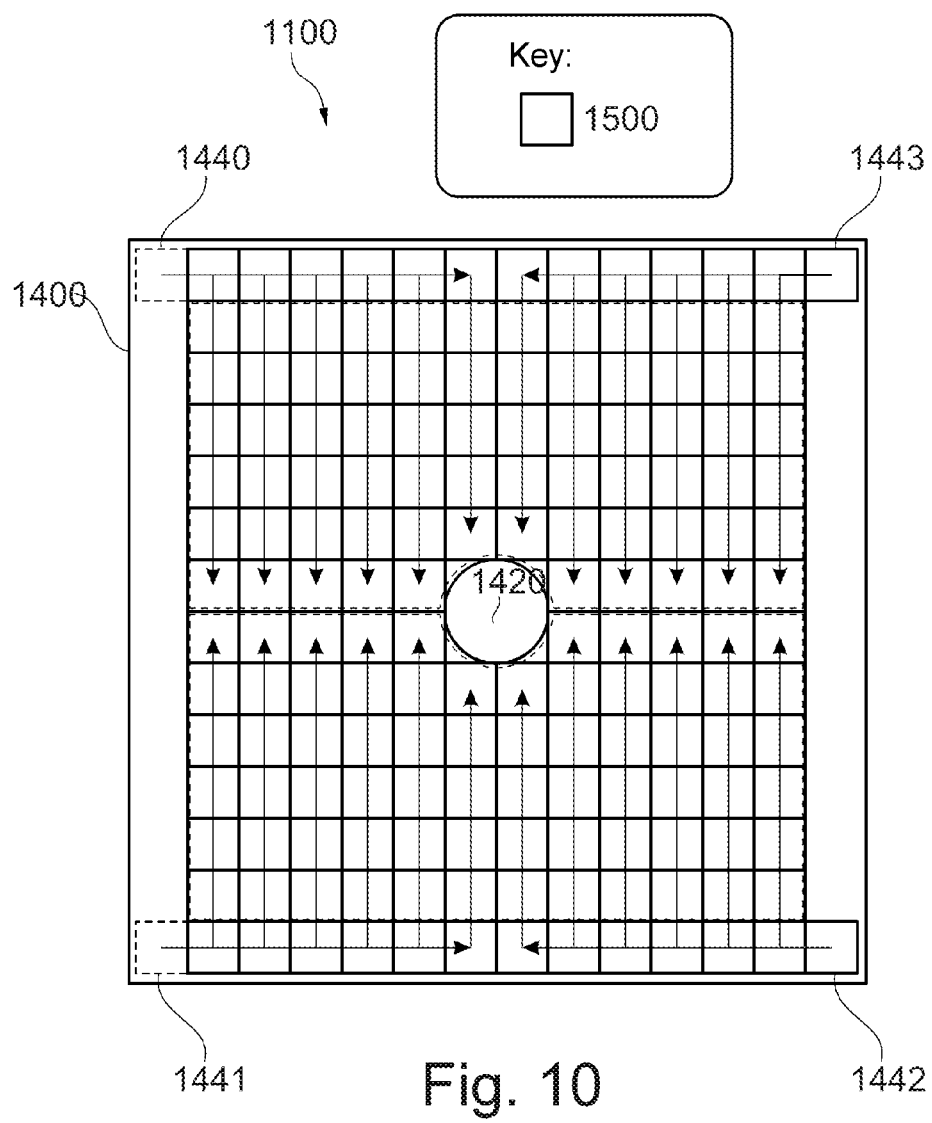
FIG. 10 shows a further embodiment of a device which facilitates an examination modality.

FIG. 10 shows a further embodiment of an device 1100, i.e., a development of the device in FIGS. 9A, 9B.

Four input coupling elements 1440 to 1443 are present in the device 1100 of FIG. 10. The multiplicity of expansion elements 1500 are coupled in such a way with one another here that a light distribution such as the light distribution 1200 in FIG. 7A can be provided by the multiplicity of expansion elements 1500.

It may be advantageous to individually adapt the above-described devices 100, 1100 for individual users or groups of users. Such methods are described below in the context of FIG. 6.

Figure 6:
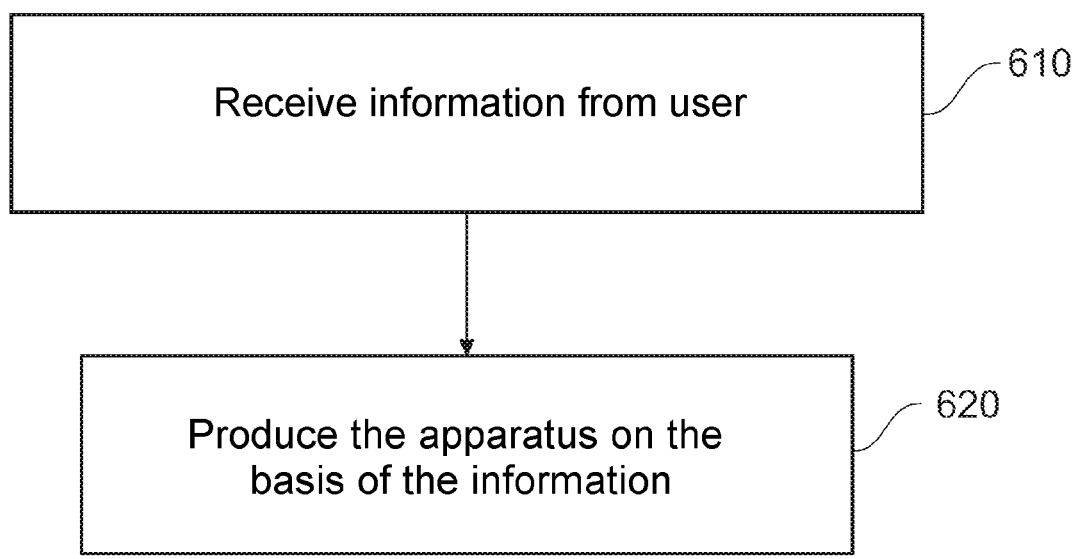
FIG. 6 shows a flowchart for a method according to various embodiments.

FIG. 6 shows a flowchart for a method according to various embodiments.

In this case, a method for producing a user-specific pair of spectacles is described.

Head geometry information relating to the user is received at 610.

The head geometry, in particular head width and interpupillary distance, vary significantly from user to user. Therefore, it may be advantageous to provide frames of different width to different users and to edge the spectacle lens in user-specific fashion. By way of example, the frames can be used to arrange the light sources 300 shown in FIGS. 3A, 3B, 4A, 4B and 5 therein. In order to each time realize aesthetic frames for different head geometries it may be advantageous to vary geometric parameters and optical properties of the device. By way of example, it is possible to vary the horizontal distance from the eye of the light source housed in the temple.

An device as described above is produced on the basis of the head geometry information at 620.

In this case, the above-described devices can be configured in such a way that such an adjustment as described at 620 can be achieved particularly easily.

In the examples where the input coupling elements, deflection elements and/or expansion elements are realized by means of volume holograms it may be possible to undertake an adjustment for an individual user by virtue of using a user-specific lateral offset of the exposure beam when producing the device, which leads to the input coupling element being written at a position suitable for the user.

As already described, the above embodiments serve merely for illustration and should not be interpreted as restrictive.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products. Moreover, features or aspects of various example embodiments may be mixed and matched (even if such combination is not explicitly described herein) without departing from the scope of the invention.

The invention claimed is:

1. A device with a spectacle lens for supplying power to an active ocular implant in an eye of a user, the device comprising:

a light source; and a beam expander arranged in or on the spectacle lens;

wherein the beam expander comprises a first expansion element and a second expansion element, wherein the device is configured to input couple light from the light source into the spectacle lens and guide the light to the first expansion element, wherein the first expansion element is configured to receive the light, expand the light along a first direction and guide at least some of the light as expanded light in a second direction to the second expansion element, wherein the second direction differs from the first direction, wherein the second expansion element is configured to receive the expanded light, expand said expanded light along the second direction and provide the expanded light as twice expanded light in a third direction via an emission surface, wherein the third direction at least partly does not extend in the spectacle lens, and wherein the second expansion element is configured to effectively focus the twice expanded light.

2. The device of claim 1, wherein effective focusing comprises steering the twice expanded light to an imaginary focal surface between the emission surface and the active ocular implant along the third direction, wherein the imaginary focal surface is smaller than the emission surface.

3. The device of claim 1, wherein the beam expander comprises a third expansion element and wherein the first expansion element is further configured to guide a further portion of the expanded light to the third expansion element in a fourth direction, wherein the fourth direction differs from the first, second and third directions, wherein the third expansion element is configured to receive the further portion of the expanded light, expand the expanded light along the fourth direction and provide the expanded light as a further portion of the twice expanded light in a fifth direction via the emission surface, wherein the fifth direction at least partly does not extend in the spectacle lens, and wherein the third expansion element is configured to effectively focus the further portion of the twice expanded light.

4. The device of claim 1, wherein the twice expanded light comprises a convergent light beam with a focal point.

5. The device of claim 4, wherein the focal point has a distance in the range of 3 mm to 50 mm from the spectacle lens.

6. The device of claim 1, further comprising a controller, wherein the controller is configured to determine a line of sight of the user, wherein the device is configured to adapt the effective focusing of the twice expanded light in response to a change in the line of sight of the eye.

7. The device of claim 6, further comprising a recording device and a scanning mirror, wherein the controller is further configured to determine the line of sight of the user based on information from the recording device and to control the scanning mirror based on the line of sight.

8. The device of claim 6, wherein the device is configured to bring about the adaptation of the effective focusing of the twice expanded light via a twist and/or a lateral displacement of an element, wherein the element comprises either the light source or a collimation optical unit.

9. The device of claim 1, wherein the device is configured to increase the effective focusing in a sixth direction, wherein the sixth direction is perpendicular to the third direction.

10. The device of claim 1, wherein the twice expanded light comprises a plurality of spatially restricted waves which each propagate at least in part from different regions of the emission surface in the third direction, wherein the plurality of spatially restricted plane waves at least partly cross and/or diverge.

11. The device as claimed in claim 10, wherein the second expansion element comprises a plurality of segments and the plurality of segments are each configured to provide one of the plurality of spatially restricted waves in each case.

12. The device of claim 1, wherein the light source comprises a laser diode with an astigmatism, and the spectacle lens is configured to undertake an anisotropic divergence adjustment of the light from the laser diode.

13. The device of claim 1, wherein the spectacle lens comprises a waveguide and transparent material, wherein the beam expander is arranged in or on the waveguide and the light from the light source is input coupled into the waveguide, and wherein the transparent material at least partly surrounds the waveguide on at least one side.

14. The device of claim 13, wherein the transparent material includes a curved part on a side of the second expansion element that faces the eye of the user, wherein the transparent material is configured to modify the effective focusing of the light by refraction.

15. The device of claim 1, wherein the spectacle lens comprises an input coupling element and an optical waveguide connected thereto, wherein the optical waveguide is configured to transmit the light to the first expansion element.

16. The device of claim 1, wherein the light source comprises at least one of the following elements:
two individual light sources which are set up to provide light in different directions and/or in different wavelength ranges and/or at different illumination positions of at least one input coupling element for input coupling the light into the spectacle lens,
a beam splitter,
a scanning mirror, and
a switchable element.

17. The device as claimed in claim 16, wherein the device is configured to switch between at least two different light distributions of light emerging from the spectacle lens depending on a line of sight of the eye.

18. The device of claim 1, wherein the spectacle lens includes a cutout.

19. A method for producing a user-specific pair of spectacles, the method comprising:
receiving head geometry information relating to the user; and
producing the device of claim 1 on the basis of the head geometry information.

20. The method of claim 19, wherein the spectacle lens comprises an input coupling element and an optical waveguide connected thereto, wherein the optical waveguide is set up to transmit the light to the first expansion element, and wherein the method further comprises:
activating a part of the spectacle lens in order to provide the input coupling element.

21. The method as claimed in claim 19, wherein the spectacle lens comprises an input coupling element and an optical waveguide connected thereto, wherein the optical waveguide is set up to transmit the light to the first expansion element, and
wherein the method further comprises determining a user-specific lateral offset for the input coupling element on the spectacle lens, and/or
wherein the input coupling element comprises an input coupling prism and the method comprises adapting the position of the input coupling prism, and/or
wherein at least two elements of the group of input coupling element, the first expansion element and the second expansion element are applied to at least two different wafers, and the method further comprises bonding the two different wafers to one another in a relative position with respect to one another, wherein the relative position is determined on the basis of the head geometry information.

22. The method of claim 19, wherein the input coupling element comprises a surface grating and/or a volume hologram, wherein the input coupling element is set up for a parameter range of head geometry information and has an input coupling surface that is larger than a light source input coupling surface of the light source on the input coupling element, and wherein the method further comprises:
positioning the light source based on the head geometry information, such that the light source input coupling surface is fixedly arranged in relation to the input coupling surface.

23. The method of claim 22, further comprising:
deactivating a portion of the input coupling surface,
wherein the deactivation is implemented by one or more of the following steps:
electrically influencing an electrical grating in the input coupling surface,
ablating a UV resist in a region of the input coupling surface,
locally introducing a material into a surface grating, wherein the material has a similar refractive index to the material of the input coupling element, and
destroying an effect of some of a hologram via electromagnetic radiation and/or temperature.

* * * * *